United States Patent
Zimnitsky et al.

(10) Patent No.: US 10,004,645 B2
(45) Date of Patent: Jun. 26, 2018

(54) RADIO OPAQUE, REDUCED-PRESSURE MANIFOLDS, SYSTEMS, AND METHODS

(71) Applicant: KCI Licensing, Inc., San Antonio, TX (US)

(72) Inventors: Dmitry Zimnitsky, San Antonio, TX (US); Neal Vail, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 858 days.

(21) Appl. No.: 14/489,208

(22) Filed: Sep. 17, 2014

(65) Prior Publication Data
US 2015/0051562 A1 Feb. 19, 2015

Related U.S. Application Data

(62) Division of application No. 13/044,212, filed on Mar. 9, 2011, now Pat. No. 8,882,730.

(60) Provisional application No. 61/313,386, filed on Mar. 12, 2010.

(51) Int. Cl.
| A61F 13/00 | (2006.01) |
| A61F 13/02 | (2006.01) |
| A61M 1/00 | (2006.01) |
| A61B 90/00 | (2016.01) |

(52) U.S. Cl.
CPC .............. *A61F 13/02* (2013.01); *A61B 90/39* (2016.02); *A61F 13/00068* (2013.01); *A61F 13/0216* (2013.01); *A61F 13/0226* (2013.01); *A61F 13/0276* (2013.01); *A61M 1/0088* (2013.01); *A61B 2090/3966* (2016.02); *A61F 2013/00536* (2013.01); *A61M 2205/32* (2013.01)

(58) Field of Classification Search
CPC ..... A61F 13/02; A61F 13/00068; A61B 90/39
USPC .................. 604/419; 427/2.1, 2.31
See application file for complete search history.

(56) References Cited

U.S. PATENT DOCUMENTS

| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |

(Continued)

FOREIGN PATENT DOCUMENTS

| AU | 550575 A1 | 3/1986 |
| AU | 745271 | 4/1999 |

(Continued)

OTHER PUBLICATIONS

RD454111A Feb. 2002 (Year: 2002).*

(Continued)

*Primary Examiner* — Cachet I Sellman

(57) ABSTRACT

A method of manufacturing a manifold pad that is, at least in part, radiopaque includes providing a manifold member having a plurality of flow channels; providing a radioopacifier; and heating the manifold member and the radioopacifier in a heating vessel at an elevated temperature to form the manifold pad. The manifold pad may distribute reduced pressure at a tissue site and allow for detection using radiography. Systems, manifold pads, and other methods are also presented.

21 Claims, 2 Drawing Sheets

(56) References Cited

U.S. PATENT DOCUMENTS

| | | |
|---|---|---|
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,718,897 A | 1/1988 | Elves |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,045,080 A | 9/1991 | Dyer et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Canon |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,649,030 B1* | 11/2003 | Tesar ................... A61F 2/0095 |
| | | 204/192.14 |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0030304 A1 | 2/2004 | Hunt et al. |
| 2005/0234336 A1 | 10/2005 | Beckman et al. |
| 2006/0079852 A1 | 4/2006 | Bubb et al. |
| 2007/0027414 A1 | 2/2007 | Hoffman et al. |
| 2007/0134163 A1 | 6/2007 | Zhao |
| 2007/0218101 A1* | 9/2007 | Johnson ................ A61B 17/88 |
| | | 424/423 |
| 2007/0275073 A1* | 11/2007 | Huey ..................... A61L 15/18 |
| | | 424/489 |
| 2008/0138387 A1 | 6/2008 | Machiraju |
| 2009/0054856 A1* | 2/2009 | Mormino ............ A61M 1/0088 |
| | | 604/313 |
| 2010/0160876 A1* | 6/2010 | Robinson ............ A61F 13/0203 |
| | | 604/319 |
| 2010/0160877 A1* | 6/2010 | Kagan ................. A61M 1/0023 |
| | | 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2005122961 A2 | 12/2005 |
| WO | 2008057600 A2 | 5/2008 |
| WO | 2008/100440 A1 | 8/2008 |
| WO | 2008100438 A1 | 8/2008 |

OTHER PUBLICATIONS

Japanese Notice of Rejection corresponding to JP2016-078101, dated Feb. 7, 2017.

Japanese Notice of Rejection for Corresponding Application No. 2016078101, dated Oct. 17, 2017.

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (and certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peŝka, "Vacuum Therapy in the Treatment of Peripheral Blood Vessels," Timok Medical Journal 11 (1986), pp. 161-164 (and certified translation).
F.E. E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

RADIO OPAQUE, REDUCED-PRESSURE MANIFOLDS, SYSTEMS, AND METHODS

RELATED APPLICATION

This application is a divisional of and claims the benefit of U.S. patent application Ser. No. 13/044,212, to Dmitry Zimnitsky, et al., entitled "Radio Opaque, Reduced-Pressure Manifolds, Systems, and Methods," filed 9 Mar. 2011, which claims the benefit, under 35 USC § 119(e), of the filing of U.S. Provisional Patent Application Ser. No. 61/313,386, entitled "Radio Opaque, Reduced-Pressure Manifolds, Systems, and Methods," filed 12 Mar. 2010, which is incorporated herein by reference for all purposes.

BACKGROUND

The disclosure herein relates generally to medical treatment systems, and more particularly, but not by way of limitation, to radio opaque, reduced-pressure manifolds, systems, and methods.

Depending on the medical circumstances, reduced pressure may be used for, among other things, reduced-pressure therapy to encourage granulation at a tissue site or for draining fluids at a tissue site. As used herein, unless otherwise indicated, "or" does not require mutual exclusivity. Both reduced-pressure therapy and drainage with reduced pressure often involve manifolding, or distributing, reduced pressure to the tissue site.

SUMMARY

According to an illustrative, non-limiting embodiment, a system for treating a tissue site on a patient includes a manifold pad, which is radiopaque, for distributing reduced pressure and for placing adjacent to the tissue site. The system further includes a sealing member for covering the manifold pad and a portion of the patient's epidermis. The system also includes a reduced-pressure source fluidly coupled to the manifold for providing reduced pressure to the manifold pad. The manifold pad includes a manifold member having an external surface area and a plurality of flow channels, and a radioopacifier deposited on the manifold member in a quantity sufficient to be detected using radiography.

According to another illustrative, non-limiting embodiment, a method of manufacturing a manifold pad that is substantially radiopaque includes the steps of providing a manifold member comprising a polymer foam and having an exterior surface, providing a radioopacifier, and heating the manifold member and the radioopacifier in a heating vessel to coat the exterior surface of the manifold member in a quantity sufficient to be detected using radiography.

According to another illustrative, non-limiting embodiment, a manifold pad for distributing reduced pressure at a tissue site includes a manifold member formed of a polymer foam and having a plurality of flow channels and a plurality of struts having a strut exterior surface. The manifold pad further includes a radioopacifier associated with the struts of the manifold member in a quantity sufficient to be detected using radiography, and the strut exterior surface of the plurality of struts is at least fifty percent (50%) covered by the radioopacifier.

Other features and advantages of the illustrative embodiments will become apparent with reference to the drawings and detailed description that follow.

DETAILED DESCRIPTION

In the following detailed description of the non-limiting, illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
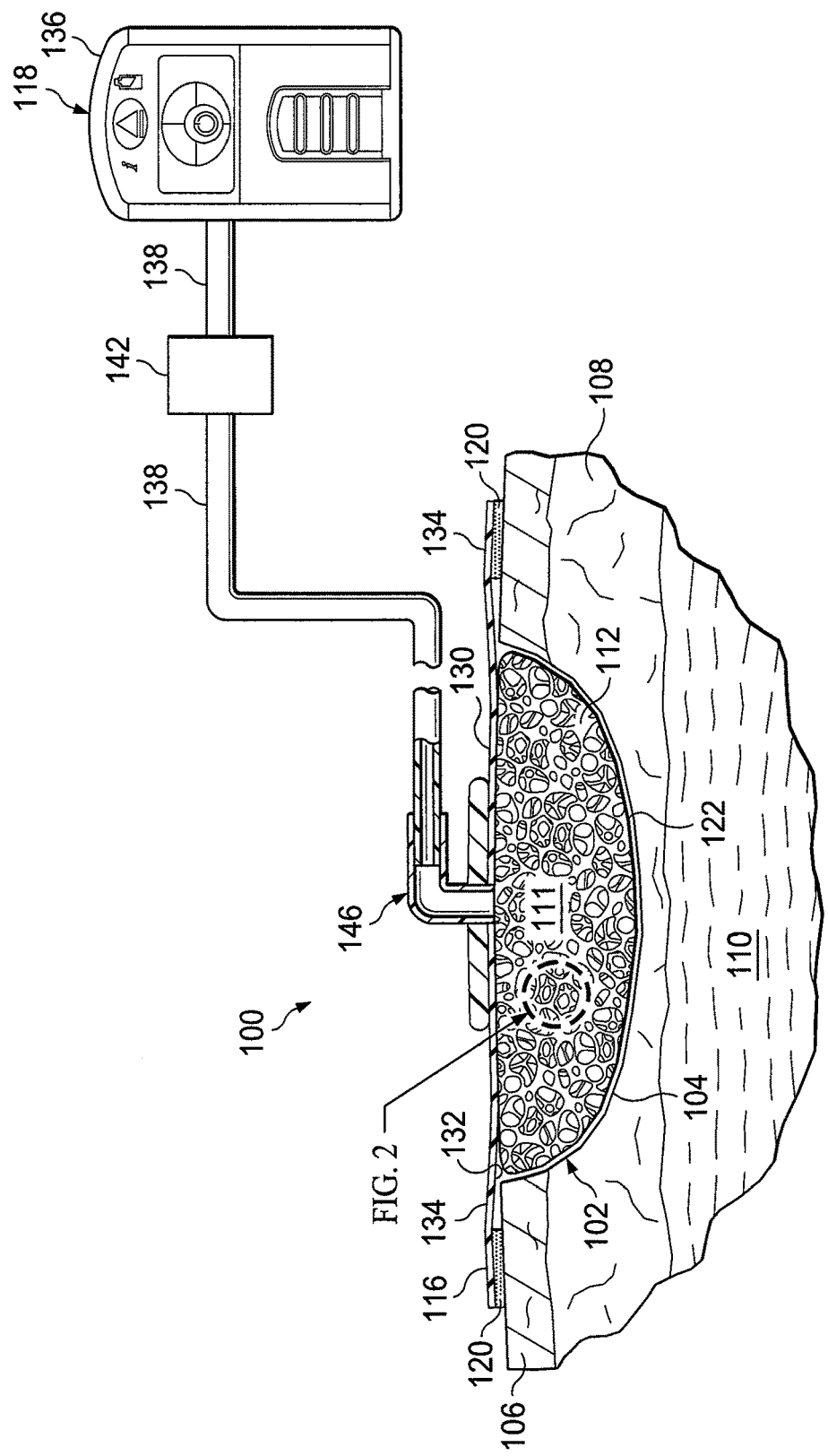
FIG. 1 is a schematic diagram with a portion shown in cross section of an illustrative, non-limiting embodiment of a reduced-pressure treatment system employing a manifold pad that includes a manifold member and a radioopacifier.
Figure 2:
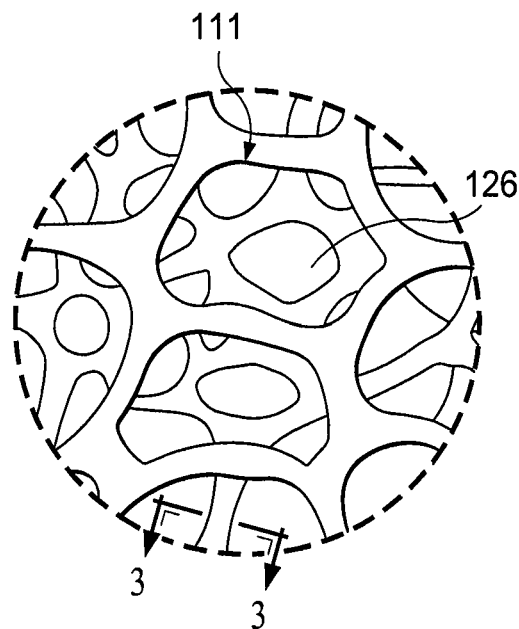
FIG. 2 is an enlarged view of area 2 in FIG. 1.
Figure 3:
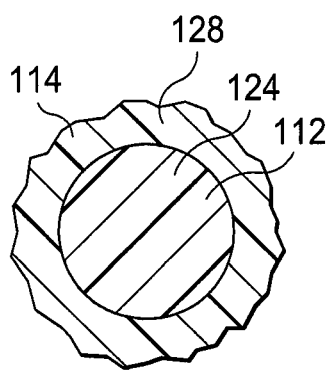
FIG. 3 is a cross sectional view of a strut from the manifold pad of FIGS. 1 and 2.

Referring now to FIGS. 1-3, a reduced-pressure treatment system 100 for treating a tissue site 102, e.g., a wound 104, is presented. The wound 104 may include, without limitation, any irregularity with a tissue, such as an open wound, surgical incision, or diseased tissue. The reduced-pressure treatment system 100 is presented in the context of a tissue site 102 that includes the wound 104, which is through the epidermis 106, or generally skin, and the dermis 108 and reaching into a hypodermis, or subcutaneous tissue 110. The reduced-pressure treatment system 100 may be used to treat a tissue, such as a wound of any depth, as well as many different types of wounds including open wounds. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue.

The reduced-pressure treatment system 100 includes a manifold pad 111, a sealing member 116, and a reduced-pressure subsystem 118. The manifold pad 111 includes a manifold member 112 and a radioopacifier 114. The manifold pad 111 is operable to distribute reduced pressure and to allow for radiopacity. Radiopacity refers to the relative inability of electromagnetism, e.g., x-rays or other radiation, to pass through a particular material. The radioopacifier 114 is associated with the manifold member 112 to make the manifold pad 111 sufficiently radiopaque to be located using radiography. For example, the radioopacifier 114 may be deposited on the manifold member 112 and thereby coupled or otherwise associated. The radioopacifier 114 may be, for example, a radio-opaque, vaporizable substance deposited on the manifold member 112 by physical vapor deposition. The manifold pad 111 will be further described below.

The sealing member 116 provides a fluid seal over the tissue site 102. "Fluid seal," or "seal," means a seal adequate to maintain reduced pressure at a desired site given the particular reduced-pressure source or subsystem involved. The reduced-pressure treatment system 100 may include an attachment device 120 for forming a fluid seal between the sealing member 116 and the patient's epidermis 106. The manifold pad 111 is positionable between a tissue-facing (inward-facing) surface 132 of the sealing member 116 and the tissue site 102. A patient-facing surface 122 of the manifold pad 111 faces the wound 104.

The term "manifold" as used herein generally refers to a substance or structure that is provided to assist in applying reduced pressure to, delivering fluids to, or removing fluids from a tissue site, e.g., tissue site 102. The manifold member 112 typically includes a plurality of flow channels or pathways to distribute fluids provided to, and remove fluids from, around the manifold member 112. The plurality of flow channels or pathways may be interconnected. The manifold member 112 may be a biocompatible material that is capable of being placed in contact with a tissue site, e.g., tissue site 102, and distributing reduced pressure to the tissue site 102. Examples of manifold members may include, without limitation, devices that have structural elements arranged to form flow channels, such as, for example, cellular foam, open-cell foam, porous tissue collections, and foams that include, or cure to include, flow channels. Thus, for example, the manifold member 112 may be porous and may be made from foam, gauze, felted mat, or other material. The manifold member 112 may be formed directly from a porous material, e.g., a foam, or from a material that is made porous, e.g., a solid member in which apertures have been applied.

In one illustrative embodiment, the manifold member 112 is a porous foam that includes a plurality of interconnected struts 124 or filaments. The struts 124 may help form a plurality of interconnected cells or pores 126, which act as flow channels through the manifold member 112. As a non-limiting example, the porous foam may be a polyurethane, open-cell, reticulated foam, such as a GranuFoam® material manufactured by Kinetic Concepts, Incorporated of San Antonio, Tex., or Granufoam Silver® material manufactured by Kinetic Concepts, Incorporated of San Antonio, Tex. As another non-limiting example, a polyvinyl alcohol foam, such as White Foam, which also available from Kinetic Concepts, Incorporated of San Antonio, Tex., might be used in some situations. The manifold pad 111, which has the radiopacifier 114, distributes (or manifolds) reduced pressure.

The sealing member 116 includes a first surface 130 and the tissue-facing (inward-facing) surface 132. The sealing member 116 may be sized so that the sealing member 116 overlaps the wound 104 in such a manner that a portion of the sealing member 116 extends beyond the periphery of the wound 104 to form an extension 134. The sealing member 116 may be any material that provides a fluid seal. The sealing member 116 may, for example, be an impermeable or semi-permeable, elastomeric material. "Elastomeric" means having the properties of an elastomer. It generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Additional, specific examples of sealing member materials include a silicone drape, 3M Tegaderm® drape, acrylic drape such as one available from Avery Dennison.

The attachment device 120 may be used to hold the sealing member 116 against the patient's epidermis 106 or another layer, such as a gasket or additional sealing member. The attachment device 120 may take numerous forms. For example, the attachment device 120 may be a medically-acceptable, pressure-sensitive adhesive that is applied to the extensions 134 of the sealing member 116. Alternatively, the pressure-sensitive adhesive may span the entire width of the sealing member 116. Alternative attachment devices may include, but are not limited to, heat-activated adhesives, sealing tapes, double-sided sealing tapes, pastes, hydrocolloids, hydrogels, hooks, or sutures.

The reduced-pressure subsystem 118 includes a reduced-pressure source 136, which can take many different forms. The reduced-pressure source 136 provides reduced pressure and may be any device for supplying a reduced pressure, such as a vacuum pump, wall suction, or other source. While the amount and nature of reduced pressure applied to a tissue site 102 will typically vary according to the application, the reduced pressure will typically be between −5 mm Hg and −500 mm Hg and more typically between −100 mm Hg and −300 mm Hg. For example, without limitation, the pressure may be −90, −100, −110, −120, −130, −140, −150, −160, −170, −180, −190, or −200 mm Hg.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. The reduced pressure delivered may be constant, varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. Unless otherwise indicated, values of pressure stated herein are gauge pressures.

A reduced-pressure conduit 138 fluidly couples the reduced pressure source 136 and a reduced-pressure interface 146. The reduced pressure developed by the reduced-pressure source 136 is delivered by the reduced-pressure conduit 138 to canister 142 and to a reduced-pressure interface 146. In one illustrative embodiment, the reduced-pressure interface 146 is a TRAC® technology port available from Kinetic Concepts, Inc. of San Antonio, Tex. The reduced-pressure interface 146 allows the reduced pressure to be realized within an interior portion below the sealing member 116 and realized within the manifold member 112. In this illustrative embodiment, the elbow port 148 extends through the sealing member 116 to the manifold member 112, but numerous arrangements are possible.

In operation, the manifold pad 111 may be placed proximate the tissue site 102, e.g., wound 104. The sealing member 116 may be placed over the manifold pad 111 such that the extension 134 extends beyond the periphery of the wound 102. The extension 134 may be secured to the patient's epidermis 106 by the attachment device 120 in order to form a fluid seal over a portion of the patient's epidermis 106 and the manifold pad 111. The reduced-pressure interface 146 may then be applied, if not already installed. The reduced-pressure conduit 138 is used to fluidly couple the reduced-pressure interface 146 and the reduced-pressure source 136.

The reduced-pressure subsystem 118 may be activated. Under a reduced pressure, fluids will be delivered from the tissue site 102 to the manifold pad 111 and through reduced-pressure conduit 138 to canister 142. After an adequate treatment period, the sealing member 116 may be removed and the manifold pad 111 removed.

The manifold pad 111 may be difficult to remove at times because of ingrowth of tissue and that at times the manifold pad 111 is cut by the healthcare provider to fit into small portions of a tissue site 102. At times, the manifold pad 111 is cut into quite complex shapes and fitted into crevices in deep wounds. In these types of situations, assurance may be desired that all portions of the manifold pad 111 have been removed from the tissue site 102. In these instances, the radioopacifier 114 allows the healthcare provider to confirm removal of all portions of the manifold pad 111 by using radiography. When radiography is used, if any portions of the manifold pad 111 remain, the radioopacifier 114 of the manifold pad 111 will appear at a detectable level on the radiograph or other results. If portions of the manifold pad 111 remain, they may be removed using surgical intervention, e.g., sharp debridement, or other techniques.

In order to locate any remaining portions of the manifold pad 111, the manifold member 112 must be substantially covered with the radioopacifier 114. In addition, the radioopacifier 114 must be sufficiently radio opaque. The manifold member 112 has an exterior surface area, or strut exterior area, that is a portion of the manifold member 112 that touches a fluid when submerged in a fluid. The exterior surface area may be at least 50% covered, at least 70% covered, at least 90% covered, a 100% covered, or any amount between 50 and 100%. The percentage average may be determined by approximating the surface area of the exterior of the struts and determining the exterior area of struts and determining the exterior area of the struts covered by the radiopacifier. As one illustrative, non-limiting example, the struts may be photographed and measured. The surface area of the exterior of the struts may be determined and the surface area of the struts covered with the radiopacifier determined. The percentage coverage may then be determined. In FIG. 3, an exterior surface area of the struts 124 of the manifold member 112 is substantially covered with a radioopacifier 114.

The manifold pad 111 has been presented initially in the context of the reduced-pressure treatment system 100. It should be understood, however, that the manifold pad 111 could be used in other situations with or without reduced pressure. The manifold pad 111 will now be described in more detail. Numerous approaches may be taken to prepare the manifold pad 111. The temperature and time are two variables that influence the amount of radioopacifier 114 that is deposited on the manifold member 112. In addition to other possible functions, the resultant manifold pad 111 may serve as an anti-microbial member. A number of non-limiting examples related to the manifold pad 111 will now be given.

Example 1

Figure 4:
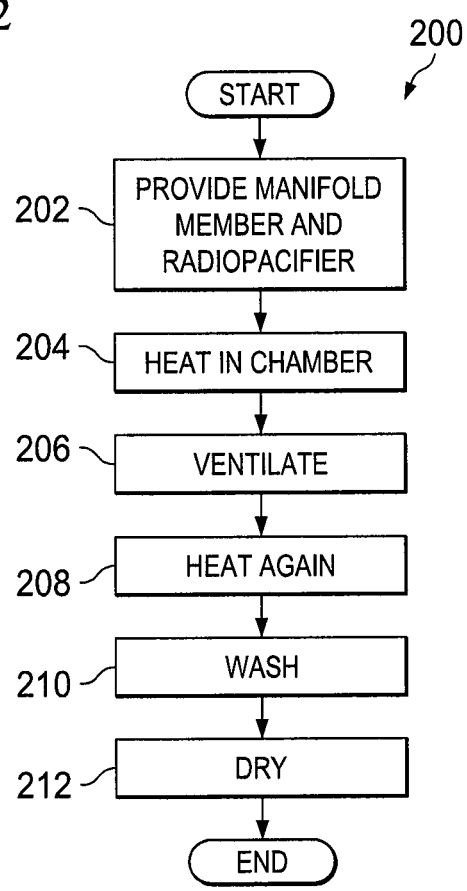
FIG. 4 is an illustrative, non-limiting embodiment of a method of manufacturing a manifold pad that includes a manifold member and a radioopacifier.

With references to FIGS. 1 to 4, and primarily to FIG. 4, one non-limiting, theoretical example of a process 200 for manufacturing the manifold pad 111 is provided. Initially, as shown at 202, the manifold member 112 and radioopacifier 114 are provided.

The manifold member 112 may be any of the materials previously mentioned for a manifold member. Additional non-limiting examples include Granufoam® material or Granufoam® silver material, which are available from KCI. A radioopacifier material 114 in vaporizable or solution-based form is then applied to the manifold member 112. For example, a molecular iodine ($I_2$) may be used as a radioopacifier, or radio-opaque, vaporizable substance.

The radioopacifier 114 (e.g., a radio-opaque, vaporizable substance) is applied using any suitable technique such as physical vapor deposition onto the manifold member 112, e.g., on to the struts 124. Thus, in the process 200, as shown at 204, the manifold member 112 and radioopacifier 114 are heated to allow for vapor deposition. The radioopacifier 114 may be applied in other ways as well. Regardless of the approach used, a portion of, or a substantial majority of the interconnected struts 124 are coated with the radioopacifier 114, e.g., >80% or >90% or >95%.

The temperature in the chamber where the manifold member 112 and radioopacifier 114 are placed is raised to an elevated temperature of about 70°-90° degrees Celsius and more typically between 80° and 90° degrees Celsius. The elevated temperature is maintained for a first time period, e.g., 3-6 hours and more typically 4-5 hours. The pressure is maintained substantially at atmospheric pressure, e.g., around 101.325 kPa at sea level.

After the first time period, as shown at 206, the manifold member 112, which now has the radioopacifier 114 associated with at least a portion of the manifold member 112, is removed and ventilated or cooled to approximately room temperature, e.g., generally in the range of 68° F. (20° C.) to 77° F. (25° C.). As suggested at 208, the manifold member 112 is then placed again in the chamber and heated to an elevated temperature typically in the range of 70° to 110° Celsius and more typically in this example to around 80° Celsius for a second time period to remove excess iodine, e.g., unbound iodine. The results of this example at this point should be around 27 to 31% (mass of the manifold pad) of iodine deposited as the radioopacifier 114 onto the manifold member 112.

The manifold member 112 may then be washed at step 210. For example, the manifold member 112 may be placed in a water wash for two or three hours. The mass loss may be monitored. The manifold member 112 with the radioopacifier 114 is then dried at step 212 and is ready to use as the manifold pad 111. The manifold pad 111 is operable to distribute reduced pressure, serve as an anti-microbial, and be radiopaque.

Example 2

In a second, non-limiting example, samples of a Granufoam® material were used as the manifold member 112. The samples were placed in a chamber with solid iodine, which was used to form the radioopacifier 114 or radio-opaque, vaporizable substance. The samples and iodine remained in the chamber for two hours at various temperatures as shown in TABLE 1. Because of the use of solid iodine, the procedure was performed in a fume hood. When taken out, the manifold members 112, which now had iodine deposited, were left to ventilate at room temperature overnight. After ventilation the samples were heated to 100° C. for 15 minutes to remove unbound iodine, or excessive iodine. The effect of temperature on the binding of iodine to Granufoam® material is shown in the TABLE 1 below. Radiography was used to verify the radiopacity of the resultant samples.

TABLE 1

| Temp. for reaction with $I_2$ | Initial manifold member weight, g | Manifold member weight after reaction with $I_2$, g | Percentage (%) of weight increase after reaction with $I_2$ | Manifold member weight after ventilation at 20° C. overnight, g | Manifold Member weight after reheating at 100° C., g | Percentage (%) of weight increase after ventilation |
|---|---|---|---|---|---|---|
| 22° C. | 0.20081 | 0.20379 | 1.5 | 0.2023 | 0.20175 | 0.5 |
| 50° C. | 0.19632 | 0.2063 | 5.1 | 0.20059 | 0.19954 | 1.6 |
| 100° C. | 0.17807 | 0.30473 | 71.1 | 0.24982 | 0.24135 | 35.5 |

Example 3

In a third, non-limiting example, samples of foam with silver, e.g., Granufoam®-Silver, were used as the manifold member 112. The samples were placed in a chamber with solid iodine as the radioopacifier 114 or radio-opaque, vaporizable substance. The samples and radio-opaque, vaporizable substance remained in the chamber for two hours at various temperatures as shown in TABLE 2. In addition to deposition of iodine, a chemical reaction occurs involving the silver and iodine to make silveriodide (AgI) salt. The salt helps keep a larger portion of the radioopacifier in place even as the manifold member 112 is washed.

When taken out, the foam samples, which now have iodine associated with them, were left to ventilate at room temperature overnight. After ventilation, the samples were heated to 100° C. for 15 minutes to remove unbound iodine, or excess iodine. The effect of temperature on the binding iodine and Granufoam® Silver material is shown in the TABLE 2. Radiography was used to verify the radiopacity of the resultant samples.

TABLE 2

| Temperature of reaction with $I_2$ | Initial Granufoam-Silver weight, g | Foam weight after reaction with $I_2$, g | Percentage (%) of weight increase after reaction with $I_2$ | Foam weight after ventilation at 20 C. overnight, g | Foam weight after Reheating at 100 C., g | Percentage (%) of weight increase after all ventilation |
|---|---|---|---|---|---|---|
| 22° C. | 0.248 | 0.2515 | 1.4 | 0.25235 | 0.25181 | 1.5 |
| 50° C. | 0.28815 | 0.29388 | 2.0 | 0.29359 | 0.29299 | 1.7 |
| 100° C. | 0.28105 | 0.37017 | 31.7 | 0.34136 | 0.33323 | 18.6 |

Example 4

In a fourth, non-limiting example, samples of Granufoam® material prepared according to examples 2 and 3 above, i.e., the reaction between Granufoam® and Granufoam® Silver with iodine as the radiopacifier 114 at 100° C., were provided. The samples were placed in deionized water for three hours. The samples were removed from the water and placed in centrifuge conical tubes with separators and centrifuged for 30 minutes at 3000 r.p.m. Then, the samples were dried at 60° C. until the mass monitoring showed that a constant weight had been realized. Naive (non-treated with iodine) manifold members, e.g., samples of Granufoam® and Granufoam®-Silver, were taken as controls. Original weights of the foams as well as weights of foams after treatment with water and drying are shown in the TABLE 3.

As TABLE 3 presents, the samples of Granufoam® material treated with iodine at 100° C. lost about 18% of their mass after treatment with water. The samples of Granufoam® Silver lost only about 3.5% of their weight. The weights of naive Granufoam® and Granufoam®-Silver materials are not affected by treatment with water. Radiography was used to verify the radiopacity of the resultant samples.

TABLE 3

| Sample | Initial foam weight, g | Dry foam weight after treatment with water, g | % of weight change |
|---|---|---|---|
| Granufoam ® | 0.02344 | 0.02361 | 0.7 |
| Granufoam ®-Iodine | 0.01987 | 0.01677 | −(18.5) |
| Granufoam ®-Silver | 0.03029 | 0.03043 | 0.5 |
| Granufoam ®-Silver-Iodine | 0.03046 | 0.02941 | −(3.6) |

The Granufoam® iodine foam initially gains weight largely because the foam physically absorbs iodine, but then part of the iodine is removed by water and so is lighter after a water rinse. In the case of Granufoam®-Silver-Iodine, in addition to physical adsorption of iodine, a chemical reaction occurs that involves the silver and iodine to make silver iodide (AGI) salt. The salt is insoluble and is not removed during washing, but other portions, e.g., absorbed portions, may be removed at least in part.

Example 5

The amount of radioopacifier 114, e.g., iodine, absorbed by the manifold member 112, e.g., foam, may be tuned, or adjusted, by varying both reaction temperature and exposure time. A fifth, non-limiting example demonstrates this effect, at least in part. Samples of foam, Granufoam® and Granufoam® Silver foams were provided. The foam samples were inserted into a chamber with iodine as the radioopacifier. The pressure in the chamber was maintained at substantially atmospheric level. Then, the foam samples were withdrawn from the chamber and ventilated according to procedure described above in Example 2.

As shown in TABLE 4, generally increasing reaction temperature and exposure time leads to higher adsorption of iodine on the foam samples. Each of the samples are treated Granufoam® Silver samples. Radiography was used to verify the radiopacity of the resultant samples. In particular, foams were placed on the skin of a pig with an X-ray film located under the animal. Images were acquired with the following X-ray parameters: 74 kVp, 76-80 mAh.

TABLE 4

| Sample # | Temperature, ° C. | Reaction time, hours | Original foam weight, g | Foam weight after iodine treatment and ventilation, g | % of weight change after treatment and ventilation |
|---|---|---|---|---|---|
| 1 | 80° | 5 | 0.15408 | 0.18506 | 20.1 |
| 2 | 80° | 8 | 0.17783 | 0.24611 | 38.4 |
| 3 | 100° | 5 | 0.17859 | 0.24709 | 38.4 |
| 4 | 100° | 8 | 0.20792 | 0.34797 | 67.4 |

Example 6

As noted earlier, the manifold pad 111 may serve to inhibit microbial growth. In a test, the antimicrobial properties of illustrative, non-limiting examples of manifold pads 111 were considered. In this example, samples of manifold pads 111 made using Granufoam® and Granufoam®-Silver foams as the manifold members 112 and iodine was used as the radioopacifier 114 were used. In the experiment, zones of inhibition of microbial growth were measured. Samples of the manifold pads 111, e.g., of the treated Granufoam® and Granufoam®-silver foams, were pre-cut into pieces of 5 mm thick and 8 mm in diameter and washed with ethyl alcohol. The weights of dried samples varied in the range of 0.009-0.01 g. The foam samples were placed in the chamber approximately three centimeters above a layer of solid iodine for two hours at 90° C. The masses of the foam samples after reaction with iodine were in the range of 0.022-0.023 g. Some of the samples were washed with sterile water for two hours and dried overnight. Weights of washed and dried samples were in the range of 0.012-0.013 g.

American Type Culture Collection (ATCC) cultures of Staphylococcus aureus (ATCC® Number #33591) (a Methicillin-resistant staphylococcus aureus (MRSA) species) and Escherichia coli (Migula) Castellani and Chalmers (ATCC® Number #10536) were re-hydrated and then streaked onto a growth plate and inoculated into a broth solution for 18 hours at 37° C. These organisms are available from the American Type Culture Collection of Manassas, Va. (www.atcc.org). The plates were incubated to reach $2\text{-}4\times10^7$ CFU/ml for each of the two strains. API identification strips were used to verify bacterial species before the test proceeded further.

The foam samples were transferred to a 100 mm plate using sterile tweezers. The foam samples were gently pressed with sterile forceps to ensure that each foam sample adhered to the agar surface. 125 µl of saline solution was administered on top of the foam samples to rehydrate and flush the antimicrobial through the foam. The plates were allowed to remain at room temperature for approximately 30 minutes. Then the plates were incubated in an inverted position for 18 hours at 37° C. After incubation, clear zones around each disk were measured. The zones where no bacterial growth occurred (zones of inhibition) correspond to the minimum concentration of drug required to inhibit bacteria growth. 30 µg of Vancomycin and 10 µg of Gentamicin were taken as standards effective G (+) and G (−) microorganisms accordingly. Average zones of inhibition are presented in TABLE 5. The manifold pads (foam samples treated with iodine in this case) show a very high antimicrobial effect—surpassing those for antibiotic standards.

TABLE 5

| | MRSA | | E. Coli | |
|---|---|---|---|---|
| Sample | Average zone of inhibition | Standard deviation | Average zone of inhibition | Standard deviation |
| Naive GranuFoam ® Control | 0 | 0 | 0 | 0 |
| Naive Granufoam ®-Silver Control | 0 | 0 | 0 | 0 |
| Vancomycin 30 ug Standard | 17.7 | 0.6 | 11.0 | 1.0 |
| Gentamicin 10 ug Standard | 19.3 | 0.6 | 26.7 | 0.6 |
| Granufoam ®-Silver-Iodine unwashed | 40.0 | 1.7 | 34.7 | 0.6 |
| Granufoam ®-Iodine unwashed | 41.0 | 0 | 38.0 | 2.6 |
| Granufoam ®-Silver-Iodine washed | 34.0 | 1.0 | 28.3 | 0.6 |
| Granufoam ®-Iodine washed | 34.3 | 1.5 | 29.3 | 1.2 |

While iodine is preferred, other radioopacifiers 114 may be used. For example, bromine, combination of iodine with bromine, and some other elements with high atomic numbers (barium salts) may provide radio opacity. While physical vapor deposition may be used and is presented in the examples, the radioopacifier may also be used in a solution-based form and applied with a wash. Some polymers with high content of iodine may be used. The polymer can be dissolved in organic solvents and applied to the Granufoam® material as a coating. Similarly, other radio dense, biocompatible materials, such as titanium, tantalum, strontium, either in metallic or associated salts, can be applied to manifold members using suitable processes to affect coating. In another illustrative, non-limiting embodiment, the manifold member may be a polyvinyl alcohol foam, such as White Foam, may be used, but the iodine or other radioopacifier would typically be applied during manufacture.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method of manufacturing a manifold pad, the method comprising:
   providing a manifold member comprising a polymer foam and having an exterior surface;
   providing a radiopacifier; and
   heating the manifold member and the radiopacifier in a heating vessel at substantially atmospheric pressure to substantially coat the exterior surface of the manifold member with the radiopacifier in a quantity sufficient to be detected using radiography.

2. The method of claim 1, further comprising washing the manifold member.

3. The method of claim 1, wherein the radiopacifier comprises molecular iodine.

4. The method of claim 1, wherein heating the manifold member comprises heating the heating vessel containing the manifold member to at an elevated temperature in the range of 60° to 110° Celsius.

5. The method of claim 1, wherein heating the manifold member comprises heating the heating vessel containing the manifold member to at an elevated temperature in the range of 70° to 90° Celsius.

6. The method of claim 1, wherein the heating vessel is heated to at an elevated temperature in the range of 60° to 110° Celsius.

7. The method of claim 1, wherein heating comprises heating the manifold member and the radiopacifier in a heating vessel for three to six hours and wherein the heating vessel is heated to at an elevated temperature in the range of 60° to 100° Celsius.

8. The method of claim 1, wherein providing a manifold member comprises providing an open-cell foam containing silver.

9. The method of claim 1, further comprising washing the manifold member after heating the manifold member, wherein the manifold member is washed for at least two hours.

10. The method of claim 1, further comprising:
    ventilating the manifold member;
    heating the manifold member a second time to remove any excess radiopacifier; and
    washing the manifold member after heating the manifold member for the second time.

11. The method of claim 1, further comprising washing the manifold member after heating the manifold member and wherein:
    providing a manifold member comprises providing an open-cell foam;
    the radiopacifier comprises molecular iodine;
    the heating vessel is heated to at an elevated temperature in the range of 60° to 110° Celsius; and
    wherein heating comprises heating the manifold member and the radiopacifier in the heating vessel for three to six hours.

12. The method of claim 1, wherein:
    the polymer foam has a plurality of flow channels and struts, and wherein the struts have a strut exterior surface area;
    the radiopacifier is iodine;
    heating comprises using physical vapor deposition to deposit the radiopacifier on the open-cell foam such that the radiopacifier covers at least seventy percent (70%) of the strut exterior surface area; and
    the method further comprises:
    washing the open-cell foam; and
    drying the open-cell foam.

13. The method of claim 12, further comprising:
    ventilating the open-cell foam after the physical vapor deposition; and
    heating the open-cell foam to remove any excess iodine.

14. A method of manufacturing a manifold, the method comprising:
    providing an open-cell polymer foam having a plurality of interconnected flow channels extending through an interior of the foam;
    providing a radiopacifier;
    heating the foam and the radiopacifier in a heating vessel to substantially coat surfaces of the interconnected flow channels with the radiopacifier;
    washing the foam.

15. The method of claim 14, wherein heating the foam comprises heating the heating vessel to an elevated temperature in the range of 60° to 110° Celsius.

16. The method of claim 14, wherein heating the foam comprises heating the heating vessel to an elevated temperature in the range of 70° to 90° Celsius.

17. The method of claim 14, wherein heating the foam and the radiopacificer comprises heating the foam and the radiopacifier in a heating vessel at substantially atmospheric pressure.

18. The method of claim 14, wherein heating comprises heating the foam and the radiopacifier in a heating vessel at substantially atmospheric pressure and wherein the heating vessel is heated to an elevated temperature in the range of 60° to 110° Celsius.

19. The method of claim 14, wherein heating comprises heating the foam and the radiopacifier in a heating vessel for three to six hours at substantially atmospheric pressure and wherein the heating vessel is heated to an elevated temperature in the range of 60° to 100° Celsius.

20. The method of claim 14, wherein the foam is washed for at least two hours.

21. The method of claim 14, further comprising:
    ventilating the foam;
    heating the foam a second time to remove any excess iodine; and
    washing the foam after heating the foam for the second time.

* * * * *